(12) United States Patent
Kuppurathanam

(10) Patent No.: US 9,126,022 B2
(45) Date of Patent: Sep. 8, 2015

(54) TEXTILE-REINFORCED HIGH-PRESSURE BALLOON

(75) Inventor: Shyam Kuppurathanam, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 706 days.

(21) Appl. No.: 12/857,068

(22) Filed: Aug. 16, 2010

(65) Prior Publication Data

US 2011/0046654 A1 Feb. 24, 2011

Related U.S. Application Data

(60) Provisional application No. 61/236,263, filed on Aug. 24, 2009.

(51) Int. Cl.
*A61M 29/00* (2006.01)
*A61M 25/10* (2013.01)
(Continued)

(52) U.S. Cl.
CPC ............ *A61M 25/10* (2013.01); *A61M 25/104* (2013.01); *A61M 25/1027* (2013.01); *D03D 1/02* (2013.01); *D03D 3/02* (2013.01); *D03D 3/06* (2013.01); *D03D 15/00* (2013.01); *A61M 2025/1031* (2013.01); *A61M 2025/1075* (2013.01); *A61M 2025/1081* (2013.01);
(Continued)

(58) Field of Classification Search
CPC ............... A61M 25/104; A61M 2025/1084; A61M 29/02; A61M 202/1084; A61M 2025/1075; A61M 2025/1081; D03D 1/02; D03D 3/02; D03D 15/00; D03D 15/08; D10D 2321/021; D10D 2321/0211; D10D 2401/061; D10D 2401/062; D10D 2401/063; D03B 1/02; D03B 15/00; D10B 2321/021; D10B 2401/062; D10B 2401/063
USPC ................... 604/96.01, 97.01, 99.01, 101.01, 604/103.01, 103.13, 103.14, 103.11, 104; 606/191–192, 194, 197–198; 623/1.13
See application file for complete search history.

(56) References Cited

U.S. PATENT DOCUMENTS

| 4,018,230 A | 4/1977 | Ochiai et al. |
| 4,327,736 A | 5/1982 | Inoue |

(Continued)

FOREIGN PATENT DOCUMENTS

| EP | 331040 A1 * 9/1989 |
| EP | 2294254 B1 * 12/2012 |

(Continued)

OTHER PUBLICATIONS

International Search Report and Written Opinion of the International Searching Authority, dated Dec. 16, 2010, 15 pages.

(Continued)

*Primary Examiner* — Katherine Rodjom
*Assistant Examiner* — Kendra Obu
(74) *Attorney, Agent, or Firm* — Brinks Gilson & Lione

(57) ABSTRACT

A textile-reinforced medical dilation balloon is provided, including a woven tubular textile sleeve with substantially longitudinal thermoplastic warp threads and at least one weft thread woven substantially perpendicular relative to the warp threads, where the sleeve defines a sleeve lumen. A medical dilation balloon is disposed within the sleeve lumen, and an adhesive coating substantially covers the inner and outer surfaces of the sleeve, attaching it to the balloon.

19 Claims, 3 Drawing Sheets

(51) Int. Cl.
  *D03D 1/02* (2006.01)
  *D03D 3/02* (2006.01)
  *D03D 3/06* (2006.01)
  *D03D 15/00* (2006.01)

(52) U.S. Cl.
  CPC . *A61M 2025/1084* (2013.01); *D10B 2321/021* (2013.01); *D10B 2331/04* (2013.01); *D10B 2401/063* (2013.01); *D10B 2509/06* (2013.01)

(56) References Cited

U.S. PATENT DOCUMENTS

| | | | |
|---|---|---|---|
| 4,559,975 A * | 12/1985 | Stits | 139/42 R |
| 4,637,396 A | 1/1987 | Cook | |
| 4,702,252 A | 10/1987 | Brooks et al. | |
| 4,706,670 A | 11/1987 | Andersen et al. | |
| 4,796,629 A | 1/1989 | Grayzel | |
| 4,896,669 A | 1/1990 | Bhate et al. | |
| 4,952,357 A | 8/1990 | Euteneuer | |
| 5,112,304 A | 5/1992 | Barlow et al. | |
| 5,192,296 A | 3/1993 | Bhate et al. | |
| 5,195,969 A | 3/1993 | Wang et al. | |
| 5,201,706 A | 4/1993 | Noguchi et al. | |
| 5,250,070 A | 10/1993 | Parodi | |
| 5,290,306 A | 3/1994 | Trotta et al. | |
| 5,314,443 A | 5/1994 | Rudnick | |
| 5,330,428 A | 7/1994 | Wang et al. | |
| 5,330,429 A | 7/1994 | Noguchi et al. | |
| 5,470,313 A | 11/1995 | Crocker et al. | |
| 5,647,848 A | 7/1997 | Jørgensen | |
| 5,772,681 A | 6/1998 | Leoni | |
| 5,827,284 A | 10/1998 | Weigum et al. | |
| 5,827,289 A | 10/1998 | Reiley et al. | |
| 5,868,708 A | 2/1999 | Hart et al. | |
| 5,868,779 A | 2/1999 | Ruiz | |
| 5,911,702 A | 6/1999 | Romley et al. | |
| 6,004,289 A | 12/1999 | Saab | |
| 6,136,258 A | 10/2000 | Wang et al. | |
| 6,156,254 A | 12/2000 | Andrews et al. | |
| 6,306,154 B1 | 10/2001 | Hudson et al. | |
| 6,423,083 B2 | 7/2002 | Reiley et al. | |
| 6,626,861 B1 | 9/2003 | Hart et al. | |
| 6,629,952 B1 | 10/2003 | Chien et al. | |
| 6,632,235 B2 | 10/2003 | Weikel et al. | |
| 6,695,809 B1 | 2/2004 | Lee | |
| 6,746,425 B1 | 6/2004 | Beckham | |
| 6,756,094 B1 * | 6/2004 | Wang et al. | 428/36.9 |
| 6,773,447 B2 | 8/2004 | Laguna | |
| 6,905,743 B1 | 6/2005 | Chen et al. | |
| 6,911,038 B2 | 6/2005 | Mertens et al. | |
| 6,977,103 B2 | 12/2005 | Chen et al. | |
| 7,156,860 B2 | 1/2007 | Wallsten | |
| 7,172,796 B2 | 2/2007 | Kinoshita et al. | |
| 7,309,324 B2 | 12/2007 | Hayes et al. | |
| 7,354,419 B2 | 4/2008 | Davies, Jr. et al. | |
| 7,682,335 B2 | 3/2010 | Pepper et al. | |
| 2002/0161388 A1 | 10/2002 | Samuels et al. | |
| 2004/0082965 A1 | 4/2004 | Beckham | |
| 2004/0109964 A1 | 6/2004 | Beckham | |
| 2004/0176740 A1 | 9/2004 | Chouinard | |
| 2005/0123702 A1 | 6/2005 | Beckham | |
| 2006/0004323 A1 | 1/2006 | Chang et al. | |
| 2006/0008606 A1 | 1/2006 | Horn et al. | |
| 2006/0009835 A1 * | 1/2006 | Osborne et al. | 623/1.13 |
| 2006/0085023 A1 | 4/2006 | Davies et al. | |
| 2006/0085024 A1 | 4/2006 | Pepper et al. | |
| 2007/0010847 A1 | 1/2007 | Pepper | |
| 2007/0016133 A1 | 1/2007 | Pepper | |
| 2007/0059466 A1 | 3/2007 | Beckham | |
| 2007/0093865 A1 | 4/2007 | Beckham | |
| 2007/0213759 A1 * | 9/2007 | Osborne et al. | 606/192 |
| 2007/0213760 A1 | 9/2007 | Hayes et al. | |
| 2007/0219490 A1 | 9/2007 | Pepper et al. | |
| 2008/0183132 A1 | 7/2008 | Davies et al. | |
| 2008/0188805 A1 | 8/2008 | Davies et al. | |
| 2008/0228028 A1 * | 9/2008 | Carlson et al. | 600/36 |
| 2009/0043254 A1 | 2/2009 | Pepper et al. | |
| 2009/0099517 A1 | 4/2009 | Steadham | |
| 2009/0157164 A1 * | 6/2009 | McKinsey et al. | 623/1.13 |
| 2009/0171440 A1 * | 7/2009 | Carlson et al. | 623/1.15 |
| 2010/0010438 A1 * | 1/2010 | Simpson | 604/96.01 |
| 2010/0179581 A1 | 7/2010 | Beckham | |
| 2010/0234802 A1 | 9/2010 | Pepper et al. | |

FOREIGN PATENT DOCUMENTS

| | | |
|---|---|---|
| GB | 1566674 A | 5/1980 |
| JP | 01-297071 | 11/1989 |
| RU | 2054953 | 2/1996 |
| WO | WO 2006086516 A2 * | 8/2006 |

OTHER PUBLICATIONS

MacRae's Blue Book, Futurematrix Interventional, www.futuremedint.com, Products Description, date unknown, 2 pages, 2008.

Bard Peripheral Vascular, "Tradition of Vascular Innovation," Product Focus, date unknown, 7 pages.

Bard Peripheral Vascular, SEC 8-K Filing, Oct. 22, 2003, 12 pages.

Pebax, Application Areas, Arkema, France, date unknown, 11 pages.

Putnam Plastics Company, "Thermoset Polymide Tubing," www.putnamplastics.com/tubing_thermoset.html, retrieved Apr. 9, 2008, 2 pages.

Bard Peripheral Vascular, "Atlas", Product Description, www.bardpv.com/_vascular/product.php?p=2, retrieved Jul. 17, 2008, 2 pages.

Bard Peripheral Vascular, "ConQuest", PTA Balloon Dilatation Catheter, Instructions for Use, date unknown, 2 pages.

* cited by examiner

TEXTILE-REINFORCED HIGH-PRESSURE BALLOON

CROSS-REFERENCE TO RELATED APPLICATIONS

This application is a non-provisional application which claims priority to U.S. provisional application Ser. No. 61/236,263, filed Aug. 24, 2009, which is incorporated by reference herein in its entirety.

TECHNICAL FIELD

The invention relates generally to minimally invasive surgical devices. More particularly, the invention pertains to a high-pressure dilatation balloon for use during a minimally invasive surgical procedure.

BACKGROUND

Balloon angioplasty is a widely used procedure for expanding constricted body passageways, such as arteries and other blood vessels, or various ducts (e.g., of the biliary system). In an angioplasty procedure, an uninflated angioplasty balloon attached to a catheter is delivered to a constricted region of a body passageway. Once the balloon is in position at the constricted region, fluid is injected through a lumen of the catheter and into the balloon. The balloon consequently inflates and exerts pressure against the constricted region to expand the passageway. After use, the balloon is collapsed, and the catheter is withdrawn. Although treatment of constricted arteries in the vasculature is one common example where balloon catheters are used, this is only one example of how balloon catheters may be used and many other uses are possible. For example, balloon catheters may also be used to temporarily occlude vessels during medical procedures to prevent blood or other fluids from flowing through a vessel. Balloon catheters may also be used to expand other intraluminal devices without dilating the surrounding vessel wall, such as stent-grafts that may be used to treat aneurysms. The above-described examples are only some of the applications in which balloon catheters are used by physicians. Many other applications for balloon catheters are known and/or may be developed in the future.

Balloons have a number of important design parameters. One is rated burst pressure, which is the statistically-determined maximum pressure to which a balloon may be inflated without rupturing. In order to expand hard, calcified lesions, it is desirable that the balloon have a rated burst pressure of at least 15 atm. It is also desirable that the balloon have a low wall thickness to minimize the profile of the delivery system. A wall thickness of about 0.03 millimeters or lower is generally preferred. For a given balloon material, however, there is a trade-off between burst pressure and wall thickness, in that the burst pressure generally decreases when the wall thickness is reduced. Accordingly, there is a need for a means of increasing the strength of balloon materials to attain higher rated burst pressures at lower wall thicknesses.

BRIEF SUMMARY

In one aspect, a textile-reinforced medical dilation balloon is provided, including a woven tubular textile sleeve with substantially longitudinal thermoplastic warp threads and at least one weft thread woven substantially perpendicular relative to the warp threads, where the sleeve defines a sleeve lumen. A medical dilation balloon is disposed within the sleeve lumen, and an adhesive coating substantially covers the inner and outer surfaces of the sleeve, attaching it to the balloon. In another aspect, a process is provided for making a textile-reinforced balloon.

DETAILED DESCRIPTION

Figure 1:
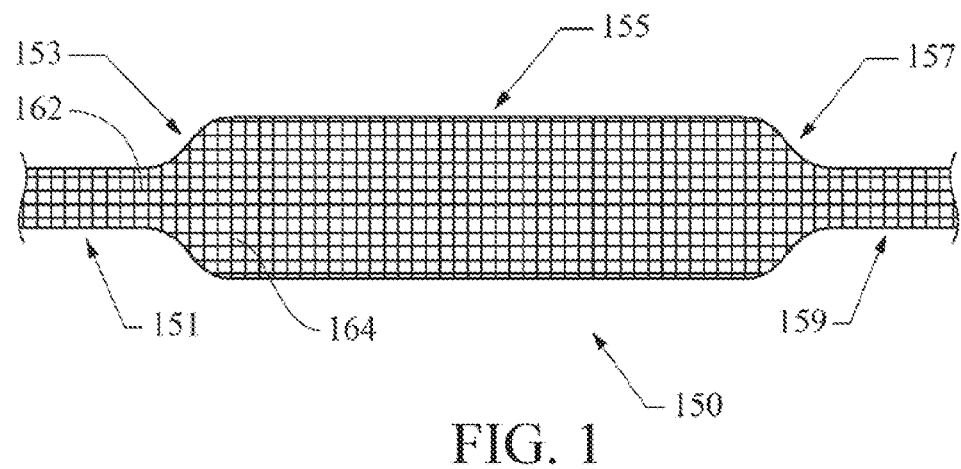
FIG. 1 is a textile sleeve.

As used herein, "proximal" refers to an end or direction associated with a physician or other treating personnel during a device operation, and "distal" refers to the opposite end ("patient end/treating end"). The term "tissue sampling device" is used generally to refer to biopsy devices. The drawing figures referred to herein are provided for illustrative purpose only. They should not be construed as limiting the scope of the invention defined by the claims, including that they may not necessarily be drawn to scale (e.g., threads of the textiles described herein and the sleeved balloons shown herein may be shown enlarged, in different size and/or numerical proportions than would occur in a physical embodiment, or may otherwise be shown diagrammatically rather than strictly literally represented for purposes of illustration and explanation).

It is desirable to provide a thin-walled balloon with a high rated burst pressure. One approach to doing so is to deposit polymer nanofibers onto a balloon's surface using an electrospinning process, such as is described in U.S. Publ. Pat. App. 2008/0157444 by Melsheimer, which is co-owned by the owner of the present application, and which is incorporated by reference herein in its entirety. However, embodiments of the presently claimed device preferably include a seamlessly woven textile sleeve around a balloon, providing a desirably thin-walled balloon device with a high rated burst pressure.

Referring to FIG. 1, a seamlessly-woven tapered textile sleeve 150 is shown, configured for use with a balloon. The sleeve 150 includes a proximal neck portion 151, a broadening proximal taper portion 153, a generally cylindrical body portion 155 defining a sleeve lumen, a narrowing distal taper portion 157, and a distal neck portion 159. A plurality of warp threads 162 run generally along the proximal-distal axis, and at least one weft thread 164 runs generally helically around, through, and along the length of the sleeve 150, woven with the warp threads 162. The at least one weft thread preferably is oriented such that it is nearly or substantially perpendicular relative to the warp threads 162 where it contacts them, rather than being disposed at an angle such as that found in a braid. It will be appreciated that, in the described woven configuration, the weft thread(s) may not be strictly perpendicular at every intersection with the warp threads, as the weft threads are substantially circumferentially or helically woven along the sleeve length, such that at least portions thereof will be angled at least slightly off of perpendicular relative to the warp threads to provide a winding pitch. However, upon visual inspection, the angle will preferably be so slight as to appear perpendicular. This construction preferably provides enhanced columnar strength and resistance to expansion of the sleeve 150 beyond a desired outer diameter (e.g., selected to correspond to a desired dilation diameter of a stricture in a lumen). The at least one weft thread 164 may be embodied as a plurality of weft threads 164.

The term "thread" as used herein includes threads, yarns, filaments, and similar structures as those terms are used in the art. The thread used may all be of the same construction, or a combination of different thread constructions and/or compositions may be used. The thread may be selected from polyester (including, for example, polyethylene terephthalate), polyethylene, and any combination thereof, although it should be appreciated that other materials may be used within the scope of the claimed invention.

One embodiment includes a plurality of polyester warp threads 162 and a single polyethylene weft thread 164 formed as a seamless tube using a plain weave (although other weaves known in the art may be used, and a seamed embodiment may be constructed). The warp thread count may be set about 50 to about 250 threads per inch (preferably about 175-200), and the weft thread count may also be set about 50 to about 250 threads per inch (preferably about 125-150). However, it should be appreciated that this range may be broadened depending upon the thread being used.

The polyester warp threads may alternatively be embodied as another thermoplastic thread such as, for example, nylon, acrylic, polystyrene, or any other thermoplastic fiber suitable for weaving and heat-bonding with a catheter (including a catheter coating of an alloy catheter such as a hypotube or multifilament/cable catheter), and the weft thread may include a polyethylene yarn, preferably having high-density, high modulus, and high tensile strength, a thermoplastic, or non-thermoplastic fiber that may be, for example, a gel-spun superstrong polyethylene fiber. In other embodiments, the warp and/or weft threads may include various grades of polyester and/or polyethylene threads, as well as other types of thread. It has surprisingly been found that using thermoplastic warp threads and one or more high-density, high modulus, and high tensile strength weft threads woven substantially perpendicularly thereto with the warp threads substantially longitudinally oriented and essentially parallel to the longitudinal sleeve axis provides a sleeve with significantly superior strength as compared to other compositions and weaves. It is thought that the relative abilities and limitations of the threads to elongate relative to each other based upon composition and orientation may contribute to this desirable effect. Individual threads may be formed of multiple fibers, including multiple types of fibers.

In certain preferred embodiments, the weft thread(s) will include at least one high-tensile-strength material and the warp threads will include at least one thermoplastic material configured to allow heat-bonding of the sleeve formed thereby to a catheter body. About 25 percent to about 100 percent, but preferably about 75 percent to about 100 percent of the weft thread(s) may be a high-tensile-strength material such as polyethylene, while the remainder may include a lower tensile strength material such as polyester, nylon, PTFE, or other material, with a preference for a higher percentage of the weft thread(s) having high tensile strength. About 25 percent to about 75 percent of the warp thread(s) may be a high-tensile-strength material such as polyethylene, while the remainder may include a lower tensile strength thermoplastic material such as polyester, nylon, PEBA, or other thermoplastic material, with a preference for at least about 40 percent of the warp thread(s) including thermoplastic material. It should be appreciated that this percentage of thermoplastic thread may be varied according to a desirable degree of heat-bonding with a particular polymer exterior of a catheter.

Warp threads preferably are selected from thermoplastic materials providing for a generally smooth weave. Weft threads preferably are selected from materials with high tensile strength and low stretchability/compliance/elasticity. In order to provide a sleeved balloon with a high rated burst pressure, it is desirable to provide a high columnar strength. In addition, for sleeved balloons used to dilate stenosed or otherwise constricted lumens (e.g., vascular lumens, ducts), it is preferable that the sleeved balloon have a consistent maximum outer diameter along its cylindrical body portion. For example, it is generally desirable that the sleeved balloon not have bulges and narrowed regions, unless it is specifically configured to have a controlled non-cylindrical outer shape to conform to a particular body structure or pre-determined shape. As such, it is preferable that the sleeved balloon be substantially non-compliant, with a pre-determined maximum effective outer diameter achieved upon full inflation. Also, those of skill in the art will appreciate that, during weaving of a tube, loom tensions may need to be adjusted along the length of the tube to maintain a desired outer diameter.

The thermoplastic properties of the preferred warp threads provide for desirable thermal bonding with a catheter and/or balloon (e.g., near or at the ends of the sleeve). The high-density, high modulus, and high tensile strength properties of preferred weft threads provide for enhanced structural integrity including a high resistance to bursting of a balloon contained in a sleeve woven according to the presently-claimed principles. The combined advantages of ease of use for attachment of a sleeve to a balloon catheter and provision of a low-profile sleeved balloon with very high burst pressure have been surprising, given the general predictability of the mechanical art of weaving, and in particularly, the combination provides surprising advantages over using only one type of thread.

Figure 2A:
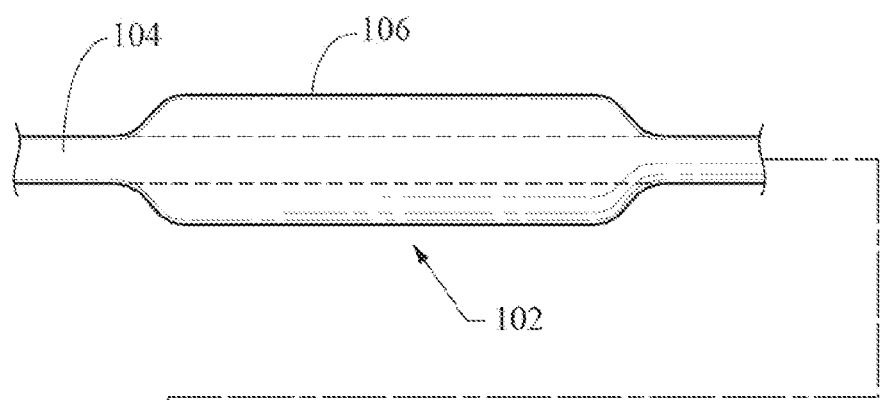
FIGS. 2A-2D show a process for making a textile-reinforced balloon.
Figure 2A:
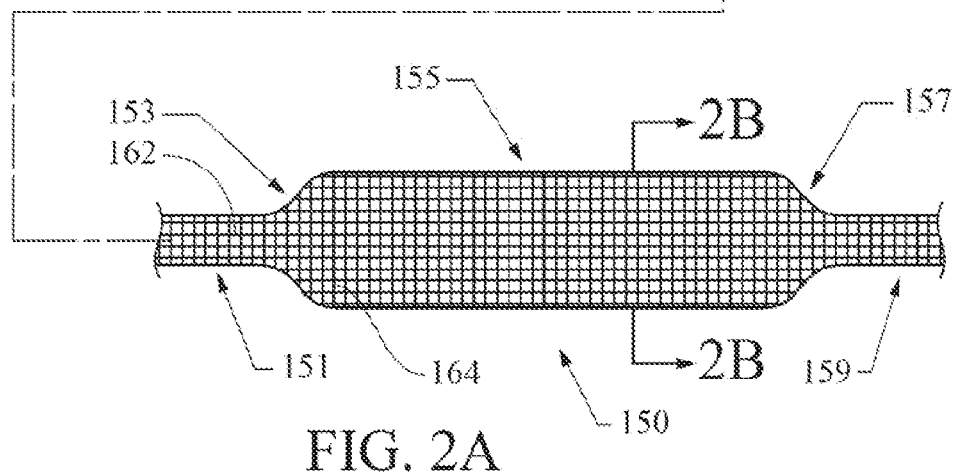

A method of assembly and the construction of a textile-reinforced (e.g., sleeved) medical dilation balloon is described with reference to FIGS. 2A-2D. FIG. 2A shows a distal section of a balloon catheter 102 including an elongate inflation catheter body 104 extending into and through the balloon lumen 108 (not visible in FIG. 2A) of a balloon 106 that preferably is a substantially non-compliant balloon. The construction of the balloon catheter 102 including connections between the catheter body 104 and balloon 106, the presence or absence of wire guide lumens, short wire/rapid-exchange structures and other construction variants may include balloon catheter constructions known in the art or developed in the future without exceeding the scope of the presently claimed invention. The balloon 106 is shown in an expanded configuration, but should be understood to be collapsible into a small generally columnar form in a manner known in the balloon art, and—during an assembly of the present device—may be inserted into the sleeve 150 in a collapsed/deflated configuration, then expanded within the sleeve 150.

Figure 2B:
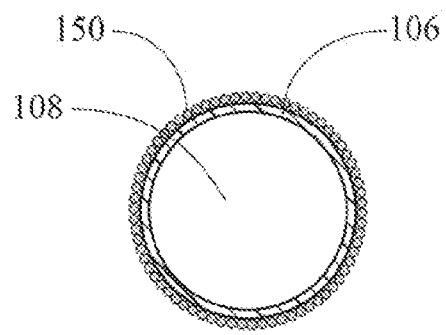
Figure 2C:
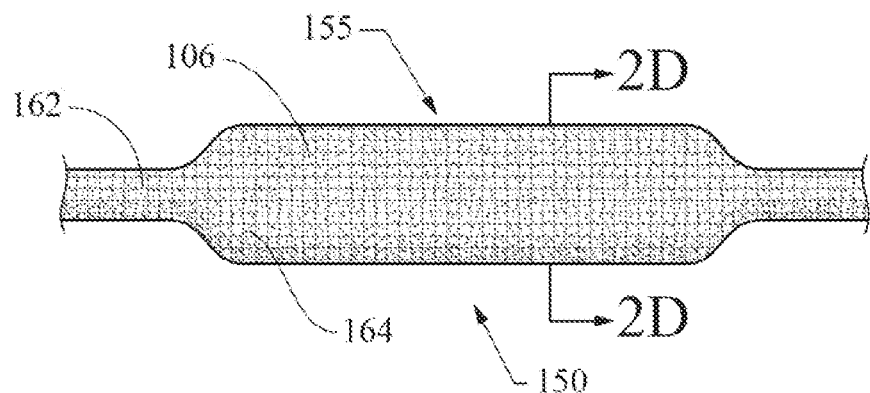
Figure 2D:
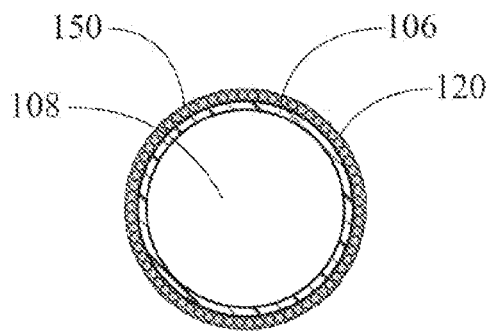

The balloon catheter 102 is shown being inserted into the sleeve lumen of the sleeve 150. The balloon 106 and the sleeve 150 preferably are dimensioned with generally the same length and tapering proportions, and the outer diameter of the balloon 106 may be about the same as the inner diameter of the sleeve lumen. In certain preferred embodiments, the balloon 106 may be slightly oversized, exceeding one or more of the inner dimensions of the sleeve lumen to provide for enhanced force of contact between the outer balloon surface and the inner sleeve surface. For example, each of the outer diameter of the balloon and the outer length of the balloon may be at least about 1 percent to at least about 35 percent (preferably at least about 20 percent) greater than the corresponding inner dimensions of the sleeve 150, with size difference of about 0.1 to about 1 mm (the percentage difference being largely size-dependent). Certain preferred embodiments are at least about 5 percent oversized in at least one dimension (e.g., diameter, length, circumference, volume). The balloon 106 may then be inflated to bring its outer surface into substantially complete full and firm, tight contact with the inner surface of the sleeve 150. FIG. 2B shows a transverse section view along line 2B-2B of FIG. 2A, illustrating the contact between the balloon 106 and the sleeve 150.

Next, the sleeve 150 may be heat-sealed to the catheter 102. Specifically, the proximal and distal sleeve necks 151, 159 may be clamped to the catheter 102 immediately proximal and distal, respectively of the aligned balloon and sleeve tapered portions, then quickly heated sufficiently (e.g., about 375° F. to about 395° F. for about 10 to about 20 seconds for polyester warp threads) to melt-seal the sleeve 150 to the body 104 (shown in dashed lines in FIG. 2) of the catheter 102, which preferably has a thermoplastic outer surface in the bonding region. For example, polyester threads of the sleeve 150 may be melt-bonded/fused to a thermoplastic (e.g., polyester, nylon, or other thermoplastic material) coating or body of the catheter 102. The weft threads may also melt-bonded or otherwise attached. In other embodiments, the ends may be attached with an adhesive or other connecting means (e.g., clamp band). This step preferably also secures the balloon 106 to the catheter 102.

Then, the sleeved balloon 106 may be dipped into an adhesive solution such as, for example, an aqueous solution of acrylic or urethane adhesive, or the adhesive solution may be applied by spraying or other appropriate means. The adhesive 120 is allowed to permeate the sleeve 150, sealing it to the surface of the balloon 106 and substantially coating the inner and outer surfaces of the sleeve 150. Heated air may then be used to dry the adhesive-coated sleeved balloon 106, shown in FIG. 2C, with a transverse section view along line 2D-2D shown in FIG. 2C. Another layer such as, for example, nylon, may be applied by dip-coating or another process to provide the balloon with a smooth/slick outer surface. This will also provide for desirable tracking behavior through body lumens and may protect the sleeve from absorbing body fluids, as well as preventing the balloon from sticking to itself.

The sleeve 150 and/or the adhesive 120 provide a safety back-up feature: in the unlikely event that a balloon 106 were to fail and rupture while inside a patient, the sleeve 150 and/or the adhesive 120 may prevent pieces of the balloon 106 from escaping inside the patient, and may lessen loss of inflation fluid in such an event. In addition, the adhesive coating presents a advantage with regard to the behavior of the coated balloon during inflation and deflation, in that the adhesive coating bonds the inner sleeve surface to the outer balloon surface such that these structures act as a single unit.

In alternative embodiments of assembly, adhesive may be applied directly to a balloon and/or the interior surface of the sleeve. This will result in somewhat different adhesion patterns and properties for the balloon that may not provide the burst strength, low-profile, and flexibility of the preferred method.

Preferably, the medical balloon formed by the process described herein achieves a rated burst pressure of equal to or greater than 30 atm. Rated burst pressure (RBP) is the statistically-determined maximum pressure to which a balloon may be inflated without rupturing. Normally, there is a 95% confidence that 99.9% of the balloons will not burst at or below the RBP upon single inflation. The medical balloon preferably has a rated burst pressure of at least 25 atm, more preferably at least 30 atm, and may also achieve a rated burst pressure of about 35 atm. It is further desirable that the medical balloon may achieve a rated burst pressure of about 40 atm. Certain preferred embodiments of balloons described herein may have an outer diameter of about 12 to about 14 mm, with an RBP of about 30 to about 35 atm and be configured for passage through a 6-7 Fr sheath. Those balloons preferably will range in length from about 15 to about 30 cm. Overall, preferred balloon embodiments in accordance with the principles and structures described herein may be about 4 to about 24 mm or greater in diameter, with an RBP of about 20 to about 40 atm, a length of about 2 to about 25 cm, and the capability of being introduced through a 5-10 Fr sheath.

EXAMPLE 1

An exemplary textile-reinforced balloon may be constructed as follows. A seamless tubular sleeve, tapered at each end, may be woven on a shuttle loom using a plain weave similar to that used in other medical textiles such as graft sleeves. The warp thread count may be set at 175 threads per inch, and the weft may be set at 150 threads per inch. The warp threads include a polyester thermoplastic fiber configured for weaving and heat-bonding with a catheter (e.g., a thermoplastic catheter coating or body), and the weft thread includes an ultrahigh molecular weight polyethylene yarn, having high-density, high modulus, and high tensile strength, that is formed including gel-spun superstrong polyethylene fiber (e.g., commercially available, proprietary polyethylene fiber formulations). After the tubular sleeve is formed, an appropriately sized (having about the same length as the expanded portion of the tapered tube, with similarly tapered proximal and distal ends), substantially non-compliant nylon balloon mounted onto a nylon-surfaced balloon catheter may be directed into the lumen of the tubular sleeve. The balloon has an expanded outer diameter that is about 5 percent greater than the inner diameter of the expanded sleeve lumen to assure good contact therebetween. The balloon will be inflated to fully and firmly contact the inner surface of the sleeve. The proximal and distal ends of the sleeve will be clamped to the catheter and heated at about 380° C. for about 15 seconds to form a secure melt-seal of the sleeve and of the balloon to the nylon catheter body. The expanded, sleeved balloon will then be dipped into an aqueous/acrylic solution, allowing the sleeve to be soaked through to fully coat the sleeve with acrylic as an adhesive, adhering it to the balloon to form a unitary structure. The sleeved balloon will then be dried in a stream of heated air, after which it will be deflated to contract its outer diameter in a manner known for processing balloons to make them ready for introduction through a guide catheter or other means for use in a dilatation procedure.

Figure 3:
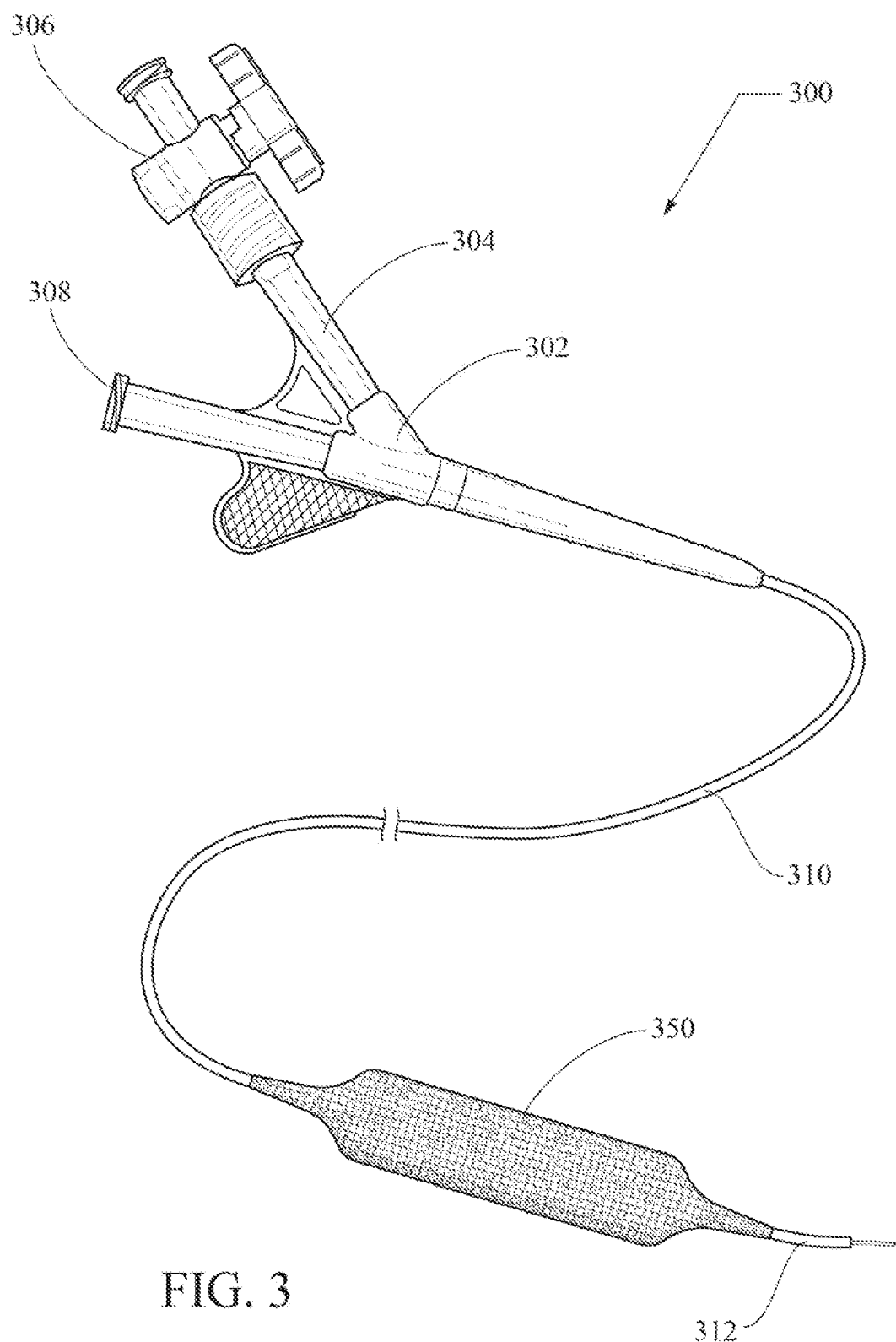
FIG. 3 shows a balloon catheter including a textile-reinforced balloon.

A balloon catheter device 300 is illustrated with reference to FIG. 3. The device 300 includes a hub 302, a catheter shaft 310, and a textile-reinforced balloon 350. The device is illustrated as including a dual-lumen catheter shaft 310, but it should be appreciated that a single-lumen catheter (for example, of the multifilar type not requiring a wire guide for navigation), or a multi-lumen catheter may be used. The hub 302 includes an inflation port 304 equipped with a stopcock attachment 306 and a wire guide port 308. The inflation port 304 is in substantially patent fluid communication with the lumen of the balloon 350. The wire guide port 308 is in mechanical communication with the distal end 312 of the catheter shaft 310. It should also be appreciated that another wire guide port could be provided as an aperture in the side of the catheter shaft 310 to allow use of the device in a short-wire/rapid-exchange procedure, and that such wire guide aperture could be provided instead of or in addition to the wire guide port 308. The textile-reinforced balloon 350 preferably is constructed in substantially the manner described above with reference to FIGS. 1-2D, but may include different construction in accordance with the claims and the other embodiments enabled herein.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

I claim:

1. A textile-reinforced medical dilation balloon, comprising:
    a seamlessly woven tubular textile sleeve including substantially longitudinal warp threads and a single weft thread helically woven substantially perpendicular relative to the warp threads so that said single weft thread extends around, through and along a length of the sleeve with the warp threads and unidirectionally helically between and from a proximal neck portion to a distal neck portion along a winding pitch, or
    said single weft thread extends around, through and along a length of the sleeve with the warp threads and unidirectionally helically between and from a distal neck portion to a proximal neck portion along a winding pitch;
    wherein the sleeve defines a sleeve lumen,
    wherein said single weft thread comprises a high-modulus, high-tensile-strength, ultrahigh molecular weight polyethylene yarn; and
    a medical dilation balloon disposed within the sleeve lumen.

2. The balloon of claim 1, wherein said single weft thread further comprises polyethylene.

3. The balloon of claim 1, where the warp threads comprise a combination of polyester and polyethylene threads.

4. The balloon of claim 3, where at least one of the plurality of threads comprises polyethylene.

5. The balloon of claim 1, where the warp threads comprise polyethylene.

6. The balloon of claim 1, where the warp threads comprise polyester.

7. The balloon of claim 1, further comprising an adhesive coating substantially covering inner and outer surfaces of the sleeve and attaching it to the balloon.

8. The balloon of claim 7, where the adhesive coating comprises urethane or acrylic.

9. The balloon of claim 1, where the tubular textile sleeve includes a generally cylindrical central body portion and tapered end portions.

10. The balloon of claim 1, comprising a rated burst pressure of at least 30 atm.

11. The balloon of claim 1, comprising a rated burst pressure of at least 35 atm.

12. A textile-reinforced medical dilation balloon prepared by a process comprising the steps of:
    constructing a seamless woven tubular textile sleeve including substantially longitudinal warp threads and a single weft thread having a high-modulus, high-tensile-strength, ultrahigh molecular weight polyethylene yarn composition different from at least one of the warp threads and woven helically substantially perpendicular relative to the warp threads such that said single weft thread extends around, through and along the length of the sleeve with the warp threads and unidirectionally helically between and from a proximal neck portion to a distal neck portion along a winding pitch, or
    so that said single weft thread extends around, through and along a length of the sleeve with the warp threads and unidirectionally helically between and from a distal neck portion to a proximal neck portion along a winding pitch;
    wherein the sleeve defines a sleeve lumen;
    directing a medical dilation balloon disposed on an inflation catheter into the sleeve lumen; and
    heating a portion of the sleeve sufficiently to thermally bond the sleeve to the inflation catheter.

13. The balloon of claim 12, where the warp threads comprise polyester.

14. The balloon of claim 13, where the warp threads further comprise polyethylene.

15. The balloon of claim 12, where the medical dilation balloon is oversized relative to the sleeve lumen by at least about 1 percent in at least one dimension.

16. The balloon of claim 12, where an outer diameter of the medical dilation balloon is at least 5 percent oversized greater than an inner diameter of the sleeve lumen.

17. The balloon of claim 12, where a warp thread count is about 50 to about 250 threads per inch.

18. The balloon of claim 12, where a weft thread count is about 50 to about 250 threads per inch.

19. The balloon of claim 12, where the process further comprises applying an adhesive coating in a manner that substantially covers inner and outer surfaces of the sleeve and attaches it to the balloon.

* * * * *